United States Patent
Kamada et al.

(10) Patent No.: US 9,594,142 B2
(45) Date of Patent: Mar. 14, 2017

(54) MAGNETIC RESONANCE IMAGING APPARATUS AND ECHO SIGNAL MEASUREMENT METHOD

(75) Inventors: Yasuhiro Kamada, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 710 days.

(21) Appl. No.: 14/113,486

(22) PCT Filed: May 9, 2012

(86) PCT No.: PCT/JP2012/061837
§ 371 (c)(1),
(2), (4) Date: Oct. 23, 2013

(87) PCT Pub. No.: WO2012/160970
PCT Pub. Date: Nov. 29, 2012

(65) Prior Publication Data
US 2014/0055137 A1 Feb. 27, 2014

(30) Foreign Application Priority Data
May 20, 2011 (JP) ................................. 2011-113890

(51) Int. Cl.
*G01R 33/561* (2006.01)
*A61B 5/055* (2006.01)
(Continued)

(52) U.S. Cl.
CPC .......... *G01R 33/5615* (2013.01); *A61B 5/055* (2013.01); *G01R 33/4824* (2013.01);
(Continued)

(58) Field of Classification Search
CPC ............ G01R 33/5615; G01R 33/4824; G01R 33/5617; G01R 33/4826; G06T 11/006; A61B 5/055
See application file for complete search history.

(56) References Cited

U.S. PATENT DOCUMENTS 6,528,996 B1    3/2003  Sato
7,285,955 B2 *  10/2007 Roberts ................ G01R 33/561
                                              324/307
(Continued)

FOREIGN PATENT DOCUMENTS

JP    2001-112734    4/2001
JP    2006-25845     2/2006
(Continued)

OTHER PUBLICATIONS

International Search Report in PCT/JP2012/061837.
(Continued)

*Primary Examiner* — G. M. Hyder
(74) *Attorney, Agent, or Firm* — Cooper & Dunham LLP

(57) ABSTRACT

In order to improve contrast in non-orthogonal measurement without sacrificing speed, in imaging which combines a fast imaging sequence for acquiring a plurality of echo signals in one shot with non-orthogonal system measurement, the shape of a blade in which an echo train of each shot is arranged is a fan shape having the radius and the arc of a circle centered on the origin of a k space. At this time, echo signal arrangement is controlled such that an echo signal of desired TE of each fan-shaped blade is arranged in a low spatial frequency region of the k space.

9 Claims, 15 Drawing Sheets

(51) Int. Cl.
  *G01R 33/48*   (2006.01)
  *G06T 11/00*   (2006.01)
(52) U.S. Cl.
  CPC ........ *G01R 33/5617* (2013.01); *G06T 11/006* (2013.01); *G01R 33/4826* (2013.01)

(56) References Cited

U.S. PATENT DOCUMENTS

| | | |
|---|---|---|
| 2008/0068014 A1 | 3/2008 | Dannels |
| 2010/0039110 A1* | 2/2010 | Takahashi .......... G01R 33/4824 324/310 |
| 2010/0152568 A1 | 6/2010 | Kokubun |
| 2014/0361771 A1* | 12/2014 | Kamada ................. A61B 5/055 324/309 |

FOREIGN PATENT DOCUMENTS

| | | |
|---|---|---|
| JP | 2008-529642 | 8/2008 |
| JP | 2010-162332 | 7/2010 |

OTHER PUBLICATIONS

M. S. Sussman et al., "Spiral-PR: A New Polar K-Space Trajectory for Flexible Variable-Density Sampling", Proc. Intl. Soc. Mag. Reson. Med., May 7, 2005, 902.

M. Saranathan et al., "Coronary artery imaging at 3T using a novel ECG gated SSFP-Dixon sequence and a motion sensitive view ordering scheme", Proc. Intl. Soc. Mag. Reson. Med., Apr. 18, 2009, 3818.

* cited by examiner

FIG.4
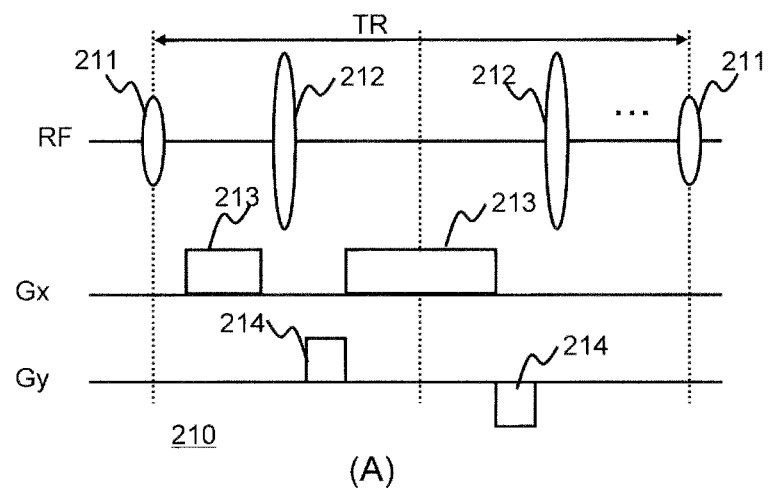
(A)
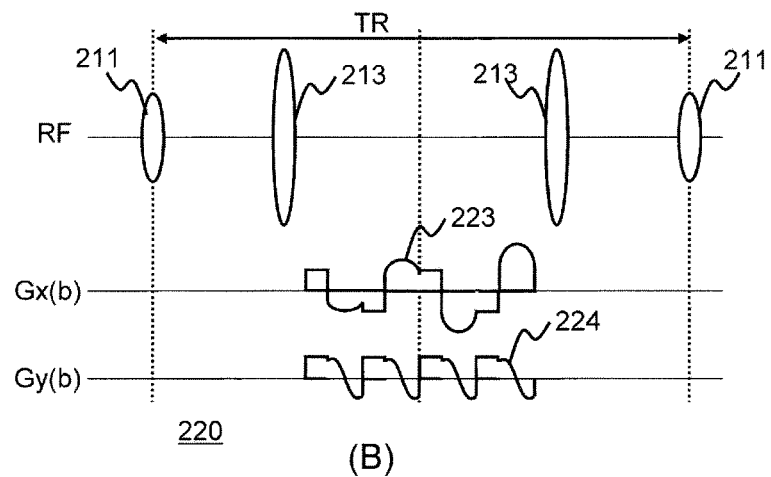
(B)

FIG.5
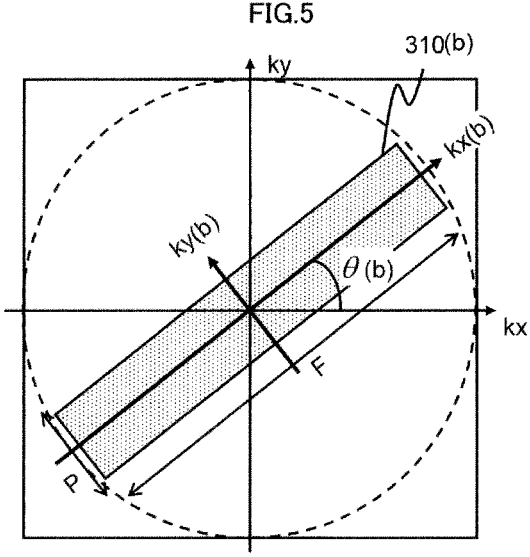
(A)
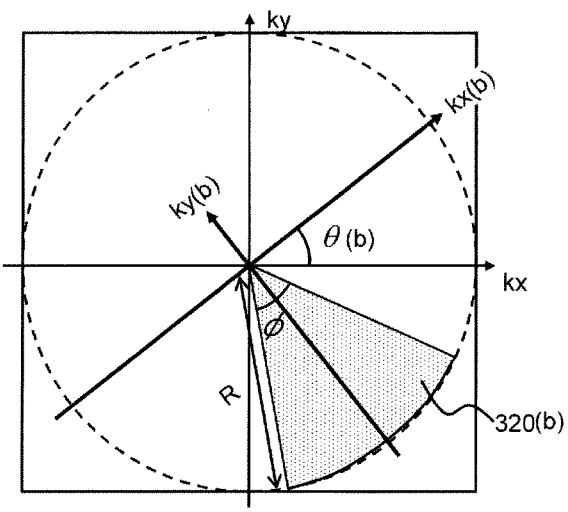
(B)

FIG.12
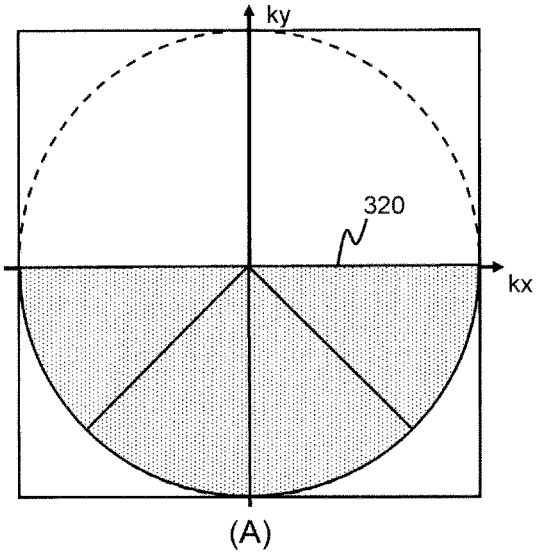
(A)
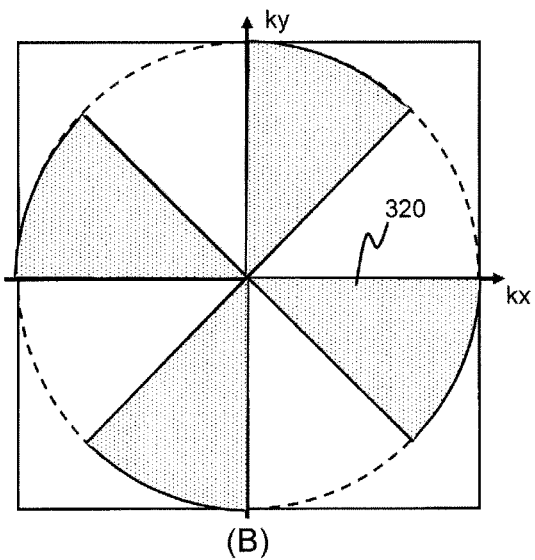
(B)

MAGNETIC RESONANCE IMAGING APPARATUS AND ECHO SIGNAL MEASUREMENT METHOD

TECHNICAL FIELD

The present invention relates to a nuclear magnetic resonance imaging (hereinafter, referred to as MRI) technology which measures a nuclear magnetic resonance (hereinafter, referred to as NMR) signal from hydrogen, phosphorus, or the like in an object and images a nuclear density distribution, a relaxation time distribution, or the like, and in particular, to a non-orthogonal system measurement technology.

BACKGROUND ART

An MRI apparatus for use in MRI is an apparatus which measures an NMR signal (echo signal) to be generated by nuclear spins constituting an object, in particular, a tissue of a human body, and images the form or function of the head, the abdomen, four limbs, or the like in a two-dimensional or three-dimensional manner. The echo signal is given different phase encode and frequency encode as positional information depending on a gradient magnetic field, and is arranged in a k space according to the positional information. The echo signal arranged in the k space is subjected to two-dimensional or three-dimensional Fourier transform, thereby reconstructing an image.

In MRI, the echo signal is measured so as to acquire data along a predetermined scan track of the k space. The scan track of the k space is classified roughly into a scan track by orthogonal system measurement which is determined by a gradient magnetic field pattern to be applied and acquires data on a k space of an orthogonal coordinate system, and a scan track by non-orthogonal system measurement which acquires data on a k space of a non-orthogonal coordinate system.

The k space of the orthogonal coordinate system is a two-dimensional or three-dimensional data space which is defined by an orthogonal two or three coordinate axes, and the k space of the non-orthogonal coordinate system is a two-dimensional or three-dimensional data space which is defined by size and declination. In the non-orthogonal system measurement, since the k space is scanned while changing the declination, near the center of the k space is repetitively scanned (for example, see NPL 1). Accordingly, this method is a robust measurement method in which the effect due to motion, such as breathing, is averaged, and no artifact is focused in a specific direction.

As an imaging method of MRI, an FSE method is known in which, after the application of a single excitation pulse, a plurality of reconvergence pulses are applied for TR until the application of the next excitation pulse to acquire a plurality of echo signals at high speed. In the FSE, the application of the single excitation pulse is referred to as a shot, and a plurality of echo signals obtained in one shot are referred to as an echo train. A method (hybrid radial method) which combines the non-orthogonal system measurement with the FSE method and obtains an image with few artifacts at high speed is known.

In the hybrid radial method, each echo train is subjected to orthogonal system measurement inside the k space of the rectangular orthogonal coordinate system referred to as a single blade, and a blade is rotated inside the k space for each shot. In this case, the major axis direction of the blade corresponds to frequency encode, and the minor axis direction of the blade corresponds to phase encode.

As a measurement method which fills the k space at high speed, an EPI method is known in which measurement is made by combining a read gradient magnetic field in a frequency encode direction and a blip gradient magnetic field in a phase encode direction. The non-orthogonal system measurement may also be combined with the EPI method. In this case, the minor axis direction of the blade is referred to as frequency encode, and the major axis of the blade is referred to as phase encode (for example, see PTL 1). By the combination of both methods, it is possible to suppress artifacts, to reduce each application time of the frequency encode gradient magnetic field, and to reduce image strain.

CITATION LIST

Patent Literature

PTL 1: U.S. Pat. No. 7,535,222

Non Patent Literature

NPL 1: Magnetic Resonance in Medicine 42:963-969 (1999). Motion Correction With PROPELLER MRI: Application to Head Motion and Free-Breathing Cardiac Imaging. James G. Pipe.

SUMMARY OF INVENTION

Technical Problem

The contrast of a reconstructed image is determined by an echo signal arranged in the central region (low spatial frequency region) of the k space. Accordingly, when a measurement method which acquires a plurality of echo signals in one shot is used, control is performed such that an echo signal having desired contrast is arranged in a low spatial frequency region (lower range). The time from the application of the excitation pulse until an echo signal having desired contrast is obtained is referred to effective TE.

On the other hand, in the non-orthogonal system measurement, since all echo signals are arranged near the lower range of the k space, an echo signal acquired for the time other than the effective TE is also arranged in the lower range of the k space. For this reason, the resultant image decreases in contrast compared to the desired contrast.

The invention has been accomplished in consideration of the above-described situation, and an object of the invention is to improve contrast in non-orthogonal measurement without sacrificing speed.

Solution to Problem

According to the invention, in imaging which combines a fast imaging sequence for acquiring a plurality of echo signals in one shot with non-orthogonal system measurement, the shape of a blade in which an echo train of each shot is arranged is a fan shape having the radius and the arc of a circle centered on the origin of a k space. At this time, echo signal arrangement is controlled such that an echo signal for desired TE of each fan-shaped blade is arranged in a low spatial frequency region of the k space.

Advantageous Effects of Invention

According to the invention, it is possible to improve contrast at high speed in non-orthogonal system measurement.

BRIEF DESCRIPTION OF DRAWINGS

FIG. 4(A) is an explanatory view illustrating an imaging sequence of the related art, and FIG. 4(B) is an explanatory view illustrating an imaging sequence of the first embodiment.

FIG. 5(A) is an explanatory view illustrating a rectangular blade of the related art, and FIG. 5(B) is an explanatory view illustrating a fan-shaped blade of the first embodiment.

FIG. 8(A) is an explanatory view illustrating centering arrangement, FIG. 8(B) is an explanatory view illustrating uncentering arrangement, and FIG. 8(C) is an explanatory view illustrating echo shift arrangement.

FIG. 12 is an explanatory view of a scan region of a k space when half measurement is applied to the first embodiment, and specifically, FIG. 12(A) is an explanatory view of semicircular half measurement, and FIG. 12(B) is an explanatory view of fan-shaped half measurement.

DESCRIPTION OF EMBODIMENTS

First Embodiment

Figure 1:
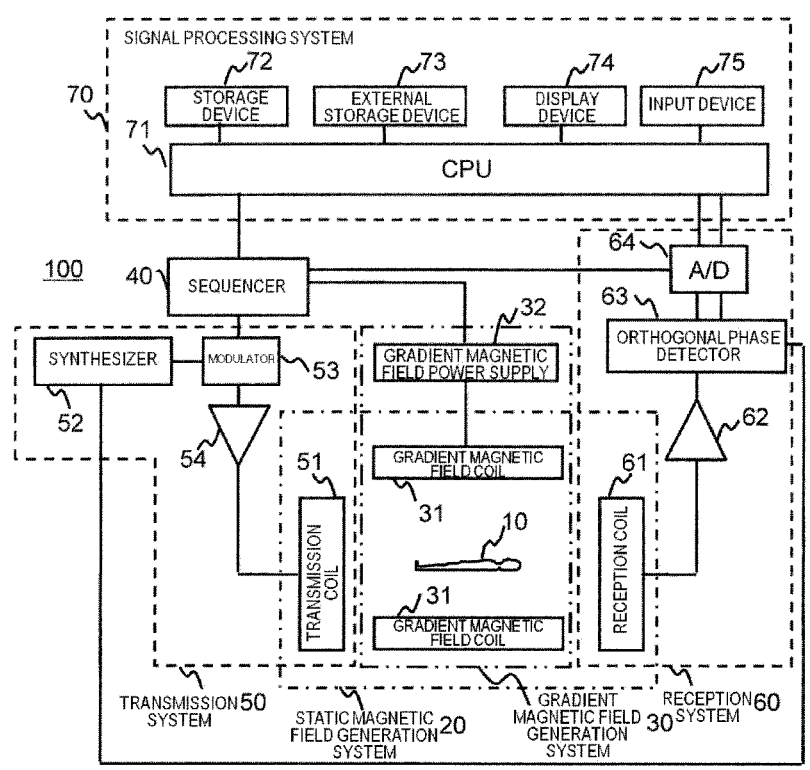
FIG. 1 is a block diagram showing the overall configuration of an MRI apparatus of a first embodiment.

Hereinafter, a first embodiment to which the invention is applied will be described. Hereinafter, in all drawings for describing an embodiment of the invention, parts having the same functions are represented by the same reference numerals, and repetitive description will be omitted.

First, the outline of an MRI apparatus 100 of this embodiment will be described referring to FIG. 1. FIG. 1 is a block diagram showing the overall configuration of the MRI apparatus 100 of this embodiment. The MRI apparatus 100 of this embodiment obtains a tomographic image of an object using an NMR phenomenon, and includes a static magnetic field generation system 20, a gradient magnetic field generation system 30, a sequencer 40, a transmission system 50, a reception system 60, and a signal processing system 70.

The static magnetic field generation system 20 generates a uniform static magnetic field in a space around the object 10 in a direction perpendicular to the body axis in the case of a vertical magnetic field system and in a body axis direction in the case of a horizontal magnetic field system, and a permanent magnet-type, normal conducting, or superconducting static magnetic field generation source is arranged around the object 10.

The gradient magnetic field generation system 30 includes gradient magnetic field coils 31 which are wound in a triaxial direction of X, Y, and Z as a coordinate system (stationary coordinate system) of the MRI apparatus 100, and a gradient magnetic field power supply 32 which drives the respective gradient magnetic field coils 31. The gradient magnetic field generation system 30 drives the gradient magnetic field power supply 32 of the respective coils according to a command from the sequence 40 described below to apply gradient magnetic fields Gx, Gy, and Gz in the triaxial direction of X, Y, and Z. During imaging, a gradient magnetic field pulse (Gs) in a slice direction is applied in a direction perpendicular to a slice surface (imaging section) to set a slice surface with respect to the object 10, and a gradient magnetic field pulse (Gp) in the phase encode direction and a gradient magnetic field pulse (Gf) in the frequency encode direction are applied in the remaining two orthogonal directions perpendicular to the slice surface to encode the positional information in the respective directions into the NMR signal (echo signal).

The sequencer 40 controls the gradient magnetic field generation system 30, the transmission system 50, and the reception system 60 so as to repetitively apply a high-frequency magnetic field pulse (hereinafter, referred to as "RF pulse") and a gradient magnetic field pulse according to a control signal from a CPU 71 provided in the signal processing system 70 described below.

The transmission system 50 irradiates the RF pulse onto the object 10 so as to excite nuclear magnetic resonance in the nuclear spins of an atom constituting a biological tissue of the object 10. The transmission system 50 includes a high-frequency oscillator (synthesizer) 52, a modulator 53, and a high-frequency amplifier 54, and a transmission-side high-frequency coil (transmission coil) 51. A high-frequency pulse output from the synthesizer 52 is amplitude-modulated by the modulator 53 at the timing according to an instruction from the sequencer 40, and the amplitude-modulated high-frequency pulse is amplified by the high-frequency amplifier 54 and supplied to the transmission coil 51 arranged near the object 10, whereby the RE pulse is irradiated onto the object 10.

The reception system 60 detects an echo signal (NMR signal) which is emitted by nuclear magnetic resonance of the nuclear spins constituting the biological tissue of the object 10. The reception system 60 includes a reception-side high-frequency coil (reception coil) 61, a signal amplifier 62, an orthogonal phase detector 63, and an A/D converter 64. An echo signal of a response of the object 10 induced by electromagnetic waves irradiated from the transmission coil 51 is detected by the reception coil 61 arranged near the object 10, then amplified by the signal amplifier 62, and divided into two systems of signals orthogonal to each other by the orthogonal phase detector 63 at the timing according to an instruction from the sequencer 40. Each of the two systems of signals is converted to a digital quantity by the A/D converter 64 and sent to the signal processing system 70.

The signal processing system 70 performs various data processes and the display, storage, and the like of the process results, and includes the CPU 71, a storage device 72, an external storage device 73, a display device 74, and an input device 75.

For example, the signal processing system 70 of this embodiment gives a control signal to the sequencer 40 according to an imaging sequence, and collects data for creating a tomographic image of the object 10 from the reception system 60. The tomographic image of the object 10 is reconstructed using collected data. The imaging sequence is generated using an imaging parameter input from an operator through the input device 75 on the basis of a pulse sequence stored in advance in the storage device 72 or the like.

Figure 2:
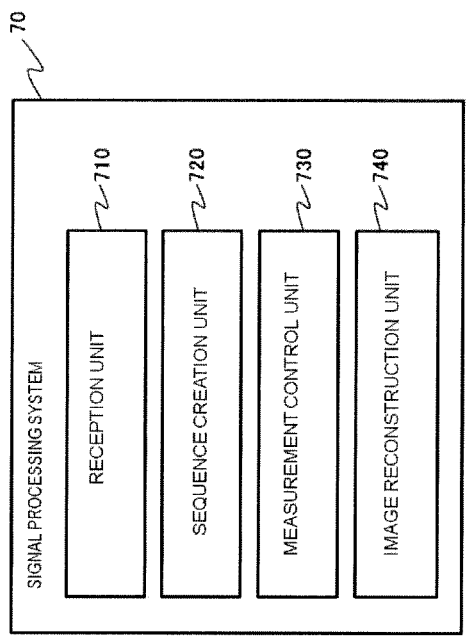
FIG. 2 is a functional block diagram of a signal processing system of the first embodiment.

In order to implement this, as shown in FIG. 2, the signal processing system 70 of this embodiment includes a reception unit 710 which receives an imaging parameter from the operator, a sequence creation unit 720 which determines a gradient magnetic field shape of a pulse sequence stored in advance using the received imaging parameter to create an imaging sequence for use in imaging, a measurement control unit 730 which measures an echo signal according to the created imaging sequence and arranges the measured echo signal in the k space, and an image reconstruction unit 740 which reconstructs an image from the echo signal arranged in the k space.

These functions are implemented when the CPU 71 loads and executes a program stored in advance in the storage device 72 or the like on a memory in the signal processing system 70.

The display device 74 displays the reconstructed tomographic image and constitutes an interface, which is used when the operator inputs various kinds of control information, along with the input device 75. The input device 75 is constituted by, for example, a trackball, a mouse, a keyboard, and the like. The storage device 72 and the external storage device store information input from the operator, information generated in the middle of the process of the signal processing system 70 and through the process, and the like.

In FIG. 1, the transmission coil 51 and the gradient magnetic field coil 31 are arranged inside the static magnetic field space of the static magnetic field generation system 20, into which the object 10 is inserted, so as to face the object 10 in the case of the vertical magnetic field system and so as to surround the object 10 in the case of the horizontal magnetic field system. The reception coil 61 is arranged so as to face or surround the object 10.

At present, in regard to the type of nucleus to be imaged by the MRI apparatus, as one which is in widespread clinical use, there is a hydrogen nucleus (proton) which is a principal component of the object. Information regarding the spatial distribution of proton density or the spatial distribution of a relaxation time of an excitation state is imaged, thereby imaging the form or function of the head, abdomen, four limbs, or the like of a human body in a two-dimensional or three-dimensional manner.

Figure 3:
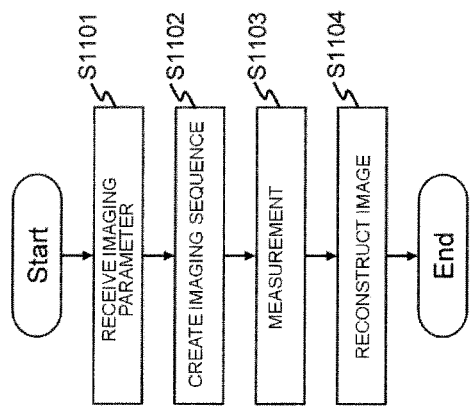
FIG. 3 is a flowchart of an imaging process of the first embodiment.

Next, the flow of an imaging process during imaging by the MRI apparatus 100 of this embodiment using each function implemented by the signal processing system 70 will be described. FIG. 3 shows a process flow of the imaging process of this embodiment.

The reception unit 710 receives the imaging parameter input by the operator through the input device 75 (Step S1101). The input imaging parameter includes a number F of frequency encodes (the number of samples in a frequency encode direction) and a number P of phase encodes (the number of samples in a phase encode direction).

The sequence creation unit 720 determines the gradient magnetic field waveform using the imaging parameter and creates the imaging sequence from the pulse sequence stored in advance in the storage device 72 or the like (Step S1102). The measurement control unit 730 gives a command to the sequencer according to the imaging sequence, measures an echo signal, and fills data in the k space (Step S1103). The image reconstruction unit 740 performs gridding on data filled in the k space on a lattice point of the orthogonal coordinate system of the k space and performs two-dimensional Fourier transform to reconstruct an image (Step S1104).

In this embodiment, as a scan region during echo signal measurement in Step S1103, a fan-shaped blade is used, instead of a rectangular blade which is used in the hybrid radial method of the related art. The k space is scanned by a plurality of fan-shaped blades. A scan track inside each fan-shaped blade is determined such that an echo signal for desired TE is arranged in the low spatial frequency region of the k space, and the shape thereof is set to be like a pendulum.

The sequence creation unit 720 determines a gradient magnetic field waveform for implementing the measurement and creates an imaging sequence. The measurement control unit 730 controls the respective units according to the created imaging sequence and executes the measurement. Hereinafter, the details of the fan-shaped blade of this embodiment and an imaging sequence creation process by the sequence creation unit 720 for implementing the above-described measurement will be described.

First, according to the related art, an imaging sequence (referred to as a related art method), in which the hybrid radial method of non-orthogonal system measurement and the FSE method are combined, and a blade on the k space measured by the imaging sequence will be described. FIG. 4(A) is an imaging sequence 210 of the related art method. FIG. 5(A) shows a rectangular region (rectangular blade) 310 on the k space measured by the imaging sequence 210 shown in FIG. 4(A). In FIGS. 4(A) and 4(B), the respective axes of RF, Gx, and Gy represent the application timing of the RE pulse and the gradient magnetic field pulses of the biaxial direction.

In the FSE method, after the application of a single excitation RF pulse 211, a plurality of reconvergence RF pulses 212 are applied for the time TR until the application of the next excitation RF pulse 211, and an echo signal is acquired each time each reconvergence RF pulse is applied. At this time, different phase encodes are given to the echo signals.

This is combined with the hybrid radial method, and for single TR (one shot), the inside of the rectangular region (rectangular blade) 310 including the origin of the k space shown in FIG. 5(A) is measured, and the measurement is repeated while changing the angle (rotation angle θ) between the rectangular blade 310 and a kx axis of the k space for each TR, thereby measuring the entire k space. In the related art method, in order to implement this, the waveforms of gradient magnetic field pulses 213 and 214 are determined. As described above, the number B (where B is a natural number) of repetitions of measurement of one rectangular blade 310 (one shot) is set as an imaging parameter by the operator.

Here, a rectangular blade (b-th rectangular blade) which is measured by b-th repetition (where b is a natural number which satisfies 1≤b≤B) is represented by 310(b). The frequency encode direction of the rectangular blade 310(b) is referred to as a kx(b) axis and the phase encode direction of the rectangular blade 310(b) is referred to as a ky(b) axis. The angle between the x axis (kx axis) and the kx(b) axis of the k space is referred to as a rotation angle θ(b) of the rectangular blade 310(b). The number F of samples in the kx(b) axis direction and the number P of samples in the ky(b) axis direction of each rectangular blade 310(b) are set as imaging parameters (the number of frequency encodes and the number of phase encodes) by the operator.

In contrast, in this embodiment, for one shot of FSE, as a unit measurement, the inside of a fan-shaped blade (unit region) having the same area (the same number of samples) as the rectangular blade 310 is measured. Then, for each shot, the unit measurement is repeated while changing the angle (rotation angle θ) between the fan-shaped blade and the kx axis, thereby measuring the entire k space having a radius R. The inside of each fan-shaped blade 320 is measured such that an echo signal having desired contrast is arranged in the low spatial frequency region of the k space. An imaging sequence 220 of this embodiment for implementing this is shown in FIG. 4(B), and the fan-shaped blade 320 of this embodiment is shown in FIG. 5(B).

As shown in FIG. 5(B), the fan-shaped blade 320 of this embodiment is a region which is surrounded by two radii R and an arc between both radii R of a circle having a radius R centered on the origin of the k space, and the central angle of the fan-shaped blade 320 is referred to as φ [rad]. It is assumed that the ky(b) axis of a b-th fan-shaped blade 320(b) is on a line (central line) which bisects the central angle φ of the fan-shaped blade 320(b). It is assumed that the kx(b) axis is a direction perpendicular to the ky(b) axis. It is assumed that the rotation angle θ(b) of the fan-shaped blade 320(b) is the angle between the kx(b) axis and the kx axis.

As shown in FIG. 4(B), similarly to FSE of the related art, the imaging sequence 220 of this embodiment applies the plurality of reconvergence RF pulses 212 for the time TR until the application of the next excitation RF pulse 211 after the application of a single excitation RF pulse 211 and acquires an echo signal each time each reconvergence RE pulse is applied. At this time, the waveforms of gradient magnetic field pulses 223 and 224 in the Gx axis and Gy axis directions are determined such that, inside the fan-shaped blade 320, data is measured with the following echo signal arrangement and scan track.

Figure 6:
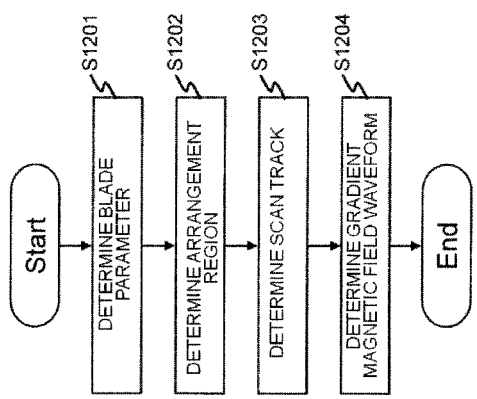
FIG. 6 is a flowchart of a gradient magnetic field shape determination process of the first embodiment.

Hereinafter, the flow of a gradient magnetic field shape determination process for determining a gradient magnetic field shape by the sequence creation unit 720 of this embodiment will be described referring to FIG. 6.

First, the sequence creation unit 720 calculates and determines the radius R, the central angle φ, and a total number $B_{fan}$ of blades as blade parameters using the imaging parameters (blade parameter determination process; Step S1201).

The total number $B_{fan}$ of blades is the number of fan-shaped blades 320 necessary for measuring the entire k space having the radius R once.

First, the radius R is defined as F/2 (R=F/2) such that the final entire sampling area becomes equal to the entire sampling area by the rectangular blade 310.

Next, the central angle φ is determined as follows.

In this embodiment, for one shot, in order to measure the inside of the fan-shaped blade 320 instead of the rectangular blade 310 of the related art, similarly to the number of samples of the rectangular blade 310, the number of samples inside each fan-shaped blade 320(b) is determined by the number F of frequency encode steps and the number P of phase encode steps set as the imaging parameters by the operator, and is represented by FP.

That is, an area S of the fan-shaped blade 320 is equal to the area FP of the rectangular blade 310. Accordingly, the area S of the fan-shaped blade 320 is expressed by Expression (1) using the number F of samples and the number P of samples.

[Equation 1]

$$S = \pi \left(\frac{F}{2}\right)^2 \frac{\phi}{2\pi} = FP \tag{1}$$

If Expression (1) is solved in terms of 4), the central angle φ is expressed by Expression (2).

[Equation 2]

$$\phi = \frac{8P}{F} \tag{2}$$

In this embodiment, the fan-shaped blade 320 is determined so as to measure the region having the radius R of the k space without overlapping in the circumferential direction. Accordingly, as shown in Expression (3), a sampling area $N_{fan}$ inside the k space measured by the fan-shaped blade 320 becomes equal to the area of a circle (radius R=F/2) which is inscribed in the space.

[Equation 3]

$$N_{fan} = \pi R^2 \tag{3}$$
$$= \frac{\pi}{4} F^2$$

Accordingly, the total number $B_f$ of the fan-shaped blades 320 is expressed by Expression (4).

[Equation 4]

$$B_{fan} = \frac{N_{fan}}{S} \tag{4}$$
$$= \frac{N_{fan}}{FP}$$
$$= \frac{\pi R^2}{FP}$$
$$= \frac{\pi}{4} \frac{F}{P}$$

Accordingly, $1 \leq b \leq B_{fan}$. This is obtained by dividing $2\pi$ by the central angle $\phi$.

Since $0 \leq \theta(b) < 2\pi$, the rotation angle $\theta(b)$ of the b-th fan-shaped blade 320 is expressed by Expression (5).

[Equation 5]

$$\theta(b) = (b-1) \times \frac{2\pi}{B_{fan}} + \Phi \tag{5}$$

Here, $\Phi$ is a constant which defines a blade rotation angle of b=1.

Next, the sequence creation unit 720 divides the fan-shaped blade 320 in a radial direction according to the number of echo signals acquired in one shot and determines an arrangement region of each echo signal inside the fan-shaped blade 320 (Step S1202).

Figure 7:
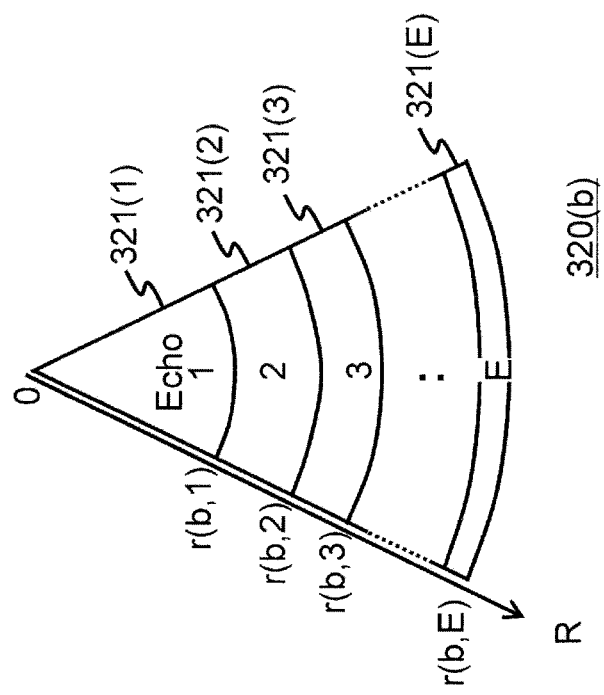
FIG. 7 is an explanatory view illustrating a divided region of the first embodiment.

Here, the number of echo signal acquired in one shot is referred to as E (where E is a natural number; E=P). As shown in FIG. 7, E echo signals are arranged in regions (divided regions) 321(n) each having the same area, (where n is a natural number which satisfies $1 \leq n \leq E$) which are obtained by dividing the fan-shaped blade 320 into E regions in the radial direction. Hereinafter, the divided regions of each b-th fan-shaped blade 320(b) are represented by 321(b,n).

In this embodiment, control is performed such that an echo signal having desired contrast is arranged in the low spatial frequency region of the k space, and other echo signals are arranged in a high spatial frequency region. Accordingly, control is performed such that an echo signal at desired timing (effective TE) is arranged in the low spatial frequency region of the divided region 321 near the origin of the k space.

The echo signal arrangement order of each divided region 321(b,n) inside the fan-shaped blade 320(b) changes depending on desired contrast. Here, for example, centering arrangement shown in FIG. 8(A) in which data is acquired in order from the central side of the k space will be described. That is, the divided region 321(b,1) where the first echo signal is arranged is defined as a radius r(b,1) of the fan-shaped blade 320(b), and the divided region 321(b,n) where the n-th echo signal is arranged is defined as a region between a radius r(b,n) and a radius r(b,n−1) of the fan-shaped blade 320(b). In the centering arrangement, r(b,E) is a radius R(b) of the fan-shaped blade 320(b).

Since the area of the divided region 321(b,n) is the same, the radius r(b,n) is represented by Expression (6).

[Equation 6]

$$r(b, n) = R(b)\sqrt{\frac{n}{E}} \tag{6}$$

Next, the sequence creation unit 720 determines a scan track inside each divided region 321n (Step S1203).

Figure 9:
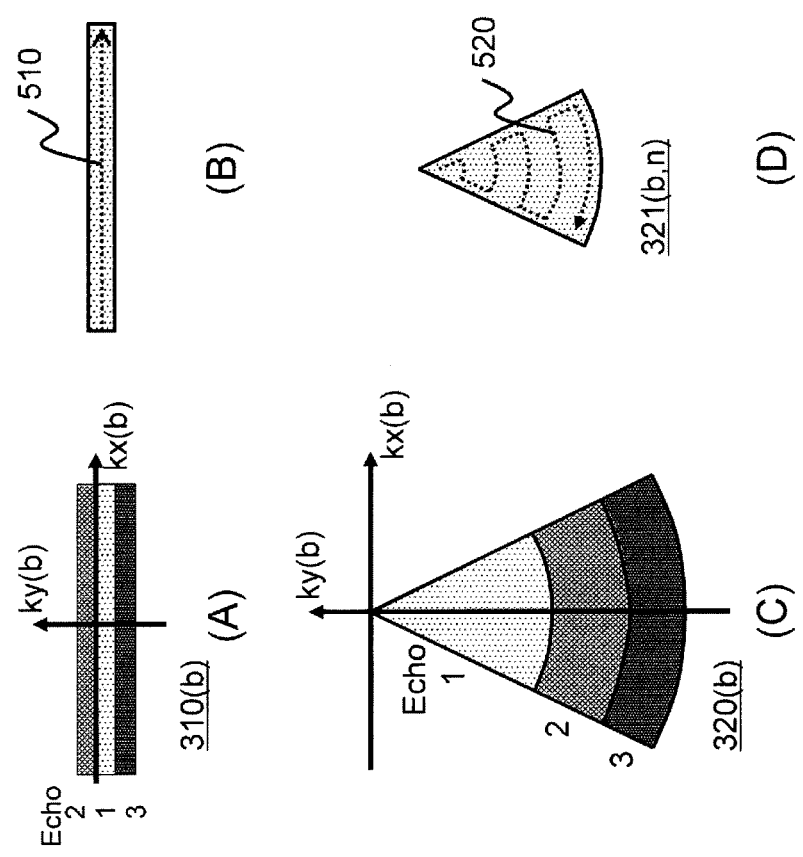
FIGS. 9(A) and 9(B) are explanatory views illustrating a scan track of an echo signal in the rectangular blade of the related art.
FIGS. 9(C) and 9(D) are explanatory views illustrating a scan track of an echo signal in the fan-shaped blade of the first embodiment.

In the rectangular blade 310(b) shown in FIG. 9(A), as shown in FIG. 9(B), one echo signal becomes a linear track (linear track 510). In this embodiment, as shown in FIG. 9(C), a scan track is set in each divided region 321(b,n) inside the fan-shaped blade 320(b). As shown in FIG. 9(D), the scan track inside each divided region 321(b,n) is a series of tracks and defines as a pendulum-like track (pendulum-like track 520) which alternately has an arc-like portion of a concentric circle to the arc of the fan-shaped blade 320 and a linear portion which connects two adjacent arc-like portions and is parallel to the radial direction.

Figure 10:
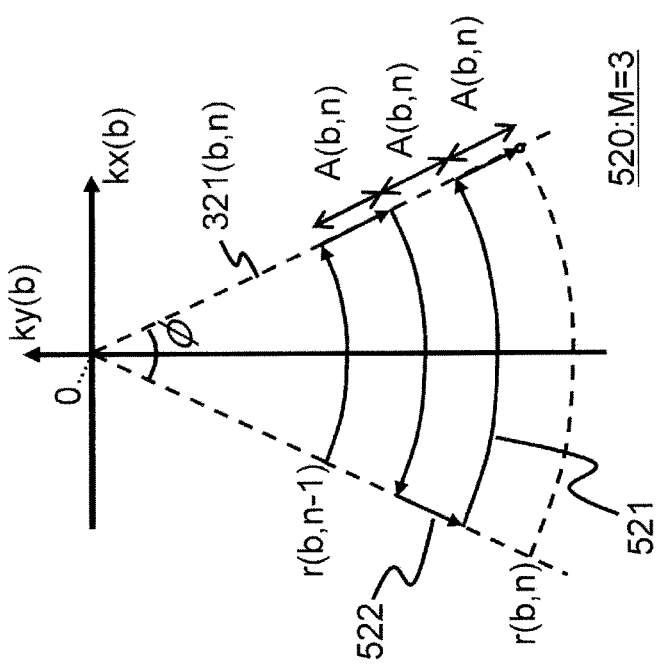
FIG. 10 is an explanatory view illustrating a pendulum-like track of the first embodiment.

In the divided region 321(b,n) of the fan-shaped blade 320(b), the number of switching times in the frequency encode direction per echo signal is defined as M(b,n). An example of the pendulum-like track 520 set inside the divided region 321(b,n) when the number M(b,n) of switching times=3 is shown in FIG. 10. As shown in this drawing, the pendulum-like track 520 is constituted by an arc-like portion (arc-like track) 521 and a linear portion (linear track) 522 which are alternately repeated M times (in this case, three times).

An interval A(b,n) between the arc-like tracks 521 corresponding to the length of the linear track 522 is expressed by Expression (7) using the radius r(b,n) of the divided region 321(b,n) of the fan-shaped blade 320(b) and the number M(b,n) of switching times.

[Equation 7]

$$A(b, n) = \frac{r(b, n) - r(b, n-1)}{M(b, n)} \tag{7}$$

A sampling length L(b,n) of the pendulum-like track 520 in each divided region 321(b,n) is the total of the arc-like tracks 521 and the linear tracks 522 of the number M(b,n) of switching times, and is thus expressed by Expression (8).

[Equation 8]

$$L(b, n) = \sum_{m=1}^{M(b,n)} (r(b, n-1) + (m-1)A(b, n))\phi(b) + \sum_{m=1}^{M(b,n)} A(b, n) \tag{8}$$

Here, m is a natural number which satisfies $1 \leq m \leq M$. Since the total sampling length of the pendulum-like track 520 inside the fan-shaped blade 320(b) is equal to the number F of samples (sampling length) in the frequency encode direction of the rectangular blade 310(b), the number M(b,n) of switching times of the divided region 321(b,n) of the fan-shaped blade 320(b) is expressed by Expression (9).

[Equation 9]

$$M(b, n) = \frac{(\phi - 2)(r(b, n) - r(b, n-1)) + 2F}{\phi(r(b, n) + r(b, n-1))} \tag{9}$$

From the above, the arc-like track 521 during m-th (a natural number which satisfies $1 \leq m \leq M$) switching in the divided region 321(b,n) of the fan-shaped blade 320(b) is expressed by Expression (10). However, $-\phi/2 \leq t \leq \phi/2$.

[Equation 10]

$$\begin{cases} kx(b) = mA(b, n)\sin((-1)^m t) \\ ky(b) = mA(b, n)\cos((-1)^m t) \end{cases} \tag{10}$$

The linear track 522 during m-th switching in the divided region 321(b,n) of the fan-shaped blade 320(b) is expressed by Expression (11). However, $(m-1)A(n) \leq t \leq mA(n)$.

[Equation 11]

$$\begin{cases} kx(b) = t\sin\left((-1)^m \dfrac{\phi(b)}{2}\right) \\ ky(b) = -t\cos\left((-1)^m \dfrac{\phi(b)}{2}\right) \end{cases} \quad (11)$$

If the arrangement region of each echo signal and the scan track are determined, the sequence creation unit 720 adds the rotation angle θ(b) of each fan-shaped blade 320(b) and determines the gradient magnetic field shape of each shot for the total number $B_{fan}$ of blades (Step S1209).

Here, the sequence creation unit 720 first creates a rotational matrix Rot(b) shown in Expression (12) using the rotation angle θ(b) of each fan-shaped blade 320(b).

[Equation 12]

$$Rot(b) = \begin{bmatrix} \cos\theta(b) & -\sin\theta(b) \\ \sin\theta(b) & \cos\theta(b) \end{bmatrix} \quad (12)$$

This is applied to the scan track of each echo signal, the scan track rotated in conformity with each fan-shaped blade 320(b) is calculated, and the waveforms of the gradient magnetic field pulses 223 and 224 in the biaxial (Gx, Gy) direction are determined.

The above-described pendulum-like track 520 is implemented by adding blip in the phase encode direction while switching the frequency encode direction during reading of one echo signal.

Through the above procedure, the sequence creation unit 720 of this embodiment determines a gradient magnetic field waveform to be measured using the imaging parameters set by the operator such that an echo signal having desired contrast is arranged in the low spatial frequency region of the k space inside the fan-shaped blade 320.

The measurement control unit 730 of this embodiment operates the respective units according to an instruction which is output from the signal processing system 70 according to the imaging sequence having the above-described gradient magnetic field waveform. That is, the rotation of each fan-shaped blade 320(b) from the kx axis by the rotation angle θ(b) and the measurement are repeated by the total number $B_{fan}$ of blades. At this time, control is performed such that an echo signal having desired contrast is arranged in the low spatial frequency region of the k space inside each fan-shaped blade 320(b). The image reconstruction unit 740 of this embodiment performs gridding on k space data obtained by the above-described measurement on the lattice point of the orthogonal coordinate system and performs two-dimensional Fourier transform to reconstruct an image.

As described above, according to this embodiment, since non-orthogonal system measurement is made, it is possible to reduce artifacts. Only a signal having desired contrast is arranged in the low spatial frequency region which determines contrast of the k space. Echo signals other than effective TE are arranged other than the low spatial frequency region. Accordingly, signals having different contrast are not mixed, and it is possible to obtain an image having desired contrast with high precision.

Accordingly, according to this embodiment, it is possible to obtain a high-quality image having few artifacts and desired contrast at high speed.

In this embodiment, the fan-shaped blade 320 is used and the region having the radius R of the k space is measured (sampled) without overlapping. Accordingly, the total number $B_{fan}$ of blades necessary for filling the perfect circular k space having the radius R (=F/2) is expressed by Expression (4). In the case of the rectangular blade 310 by the hybrid radial method of the related art, a total number $B_{rec}$ of blades necessary for filling the perfect circular k space having the radius R (=F/2) is obtained by Expression (13).

[Equation 13]

$$B_{rec} = \dfrac{\pi}{2}\dfrac{F}{P} \quad (13)$$

A sampling area $N_{rec}$ of the entire k space is expressed by (14).

[Equation 14]

$$N_{rec} = FP \times B_{rec} \quad (14)$$
$$= \dfrac{\pi}{2}F^2$$

In this way, when comparing Expression (4) and Expression (13), the number of blades necessary for scanning the area (the perfect circular k space having the radius R) of the same k space is ½ when the fan-shaped blade 320 is used compared to a case where the rectangular blade 310 is used, and the measurement time can be reduced. Accordingly, according to this embodiment, it is possible to improve filling efficiency of the k space and to reduce the measurement time.

In this embodiment, for example, a case where a combination with the FSE sequence is made has been described. However, in this embodiment, the scan region of the echo signal of each shot is defined as a fan-shaped blade, and the scan order and the scan track are determined as described above, thereby obtaining the above-described effects. Accordingly, it should suffice that the pulse sequence which is combined in this embodiment is a pulse sequence in which a plurality of echo signals are acquired for TR after the application of a single excitation pulse, and the pulse sequence can be applied without depending on a sequence type or contrast.

Figure 8:
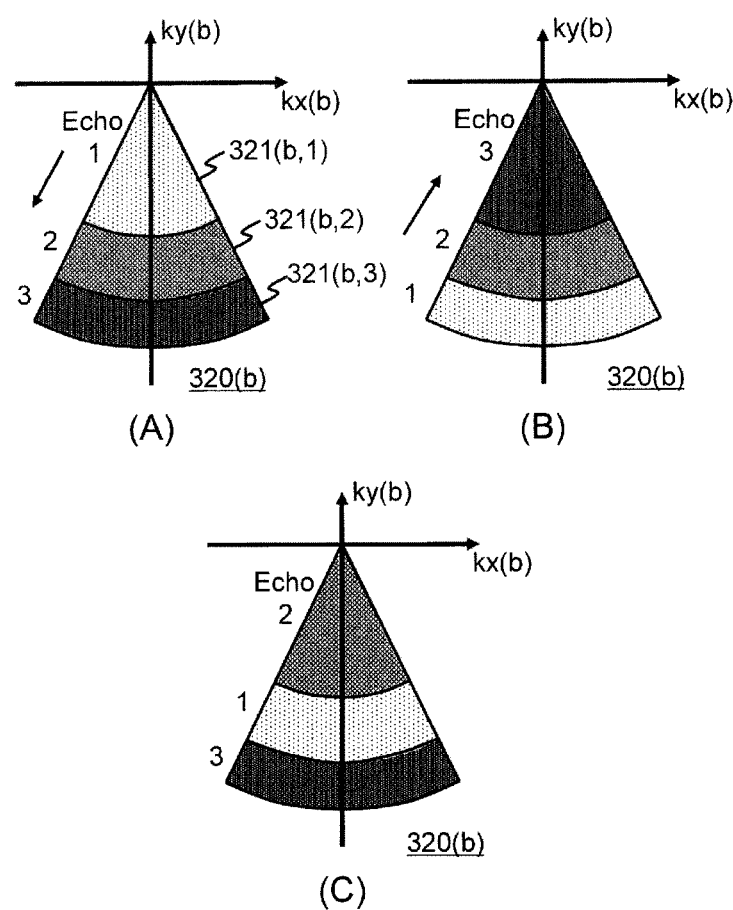
FIG. 8 is an explanatory view illustrating data arrangement of a k space, and specifically.

In the foregoing embodiment, for example, although the centering arrangement shown in FIG. 8(A) has been described, the echo signal arrangement order is not limited thereto. An echo signal for desired TE (effective TE) is determined so as to be arranged in the divided region 321 nearest the origin of the k space. With this configuration, it is possible to obtain an image having desired contrast.

For example, uncentering data arrangement shown in FIG. 8(B) in which data is acquired in order from the outer circumference may be made. An acquisition order e (1≤e≤E) of echo signals to be acquired for TR is considered. While a number n (1≤n≤E) of the divided region 321 becomes n=e in the case of the centering arrangement, the number n of the divided region 321 becomes n=E−e+1 in the case of the uncentering arrangement.

As shown in FIG. 8(C), echo shift may be applied. In this case, the divided region and the scan track are determined by the same method as described above, and the gradient magnetic field shape is determined when determining the gradient magnetic field shape of each shot in Step S1204 taking into consideration the echo arrangement order.

Figure 11:
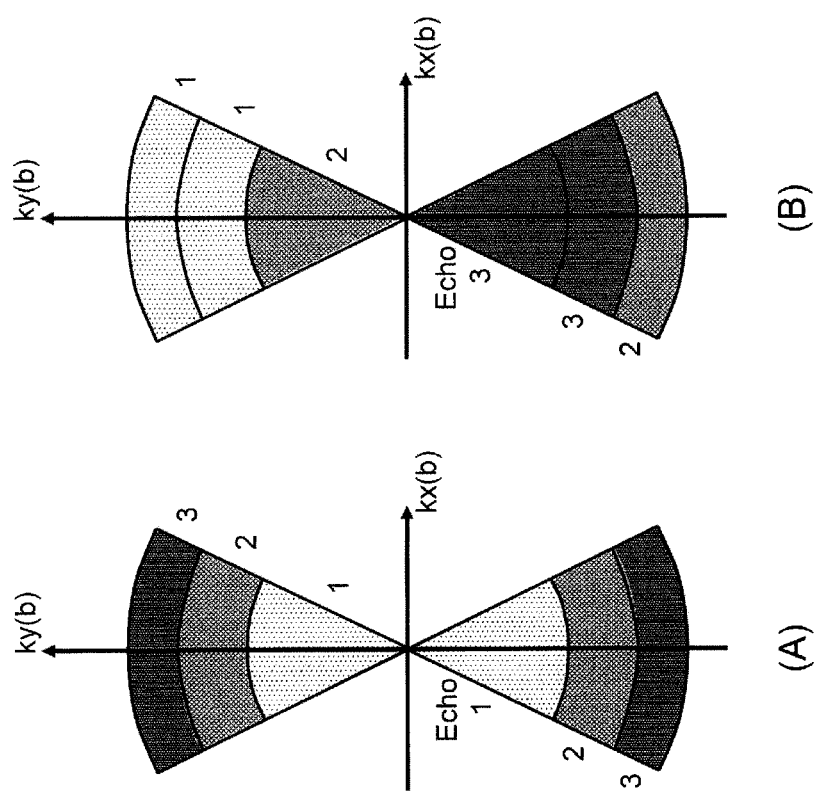
FIGS. 11(A) and 11(B) are explanatory views illustrating another example of data arrangement of the first embodiment.

When echo shift is applied, as shown in FIG. 11, two or more fan-shaped blades 320 may be used and the echo signals may be acquired in a cross-sectional manner. With this configuration, it is possible to make a measurement with a small echo signal step while allowing greater echo shift. FIG. 11(A) shows an echo signal arrangement order before echo shift, and FIG. 11(B) shows an echo signal arrangement order after echo shift. A case where the number E of echo signals is 3 is illustrated. A number next to the fan-shaped blade 320 is an echo number.

In this embodiment, multi-contrast measurement may be applied. The multi-contrast measurement is a measurement method in which two or more images having different contrast are acquired simultaneously by single measurement. For example, the multi-contrast measurement is implemented by acquiring two or more echo signals with a single pulse sequence and filling these echo signals in two or more k spaces.

The multi-contrast measurement is well used when TR is long, and a proton density weighted image (POW) and a T2 weighted image (T2W) are acquired simultaneously. Since the POW uses short effective TE, centering echo signal arrangement is used. Since the T2W uses comparatively long TE, uncentering or echo shift is used. When number of echo shifts when echo shift is used is automatically calculated according to effective TE of the T2W.

In this way, when this measurement is applied to the multi-contrast measurement, optimum echo signal arrangement according to TE of each image is used.

In the foregoing embodiment, although a region inside the circle having the radius R of the k space is measured over the entire region, the invention is not limited thereto. For example, half measurement in which about a 50% region of the k space is measured and the remaining region is estimated and filled using symmetry of the k space may be applied. In the half measurement, since a region other than an actual measurement region is estimated and filled, spatial resolution is not lowered; however, the measurement time is reduced because the actual measurement region is small.

An example of an actual measurement region (scan region) of the k space when half measurement is applied to this embodiment is shown in FIG. 12.

FIG. 12(A) shows an example of semicircular half measurement in which the inside of a semicircular region in the internal region of a circle having the radius R of the k space is measured. In the semicircular half measurement, echo signals are measured only for the fan-shaped blades 320 included in a region satisfying ky≤0 inside the circle having the radius R of the k space.

FIG. 12(B) shows an example of fan-shaped half measurement. In the fan-shaped half measurement, echo signals are measured only for the odd-numbered or even-numbered fan-shaped blades 320. However, when the total number $B_{fan}$ of blades calculated by Expression (4) is odd-numbered, since a data measurement region does not correspond to an estimated region, 1 is added to $B_{fan}$ so as to be even-numbered.

This embodiment may be combined with measurement which scans inside blades having different shapes.

For example, in the case of dynamic measurement in which improvement of resolution in the time direction is required, it is necessary to increase the data acquisition frequency of the lower range portion of the k space.

Figure 13:
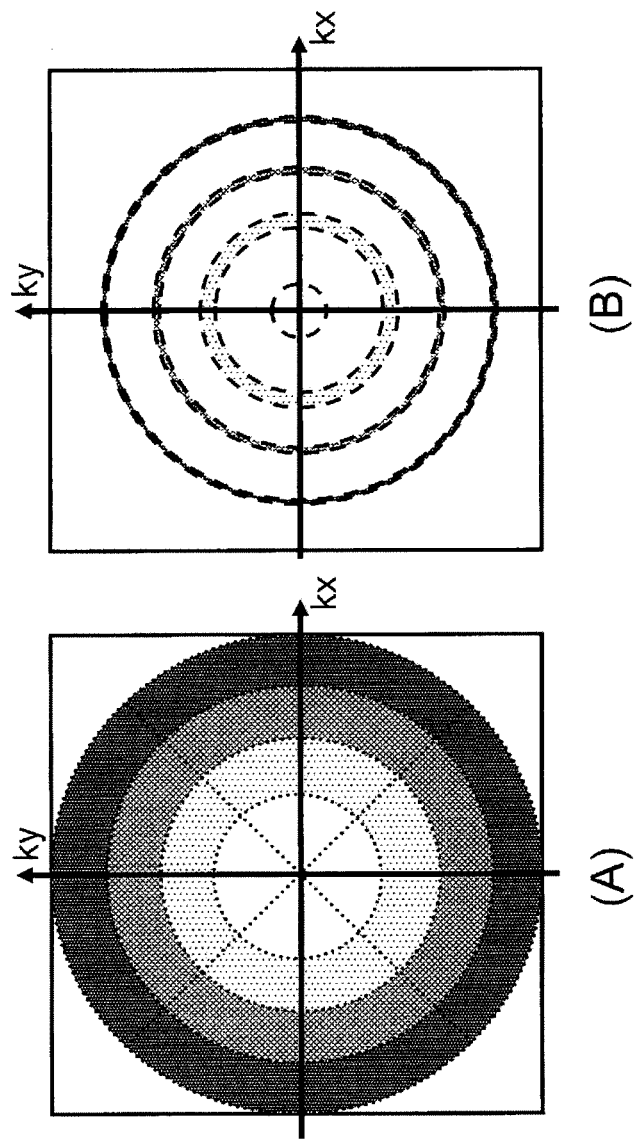
FIGS. 13(A) and 13(B) are explanatory views illustrating a measurement region when the first embodiment is combined with dynamic measurement.

First, the fan-shaped blade 320 of this embodiment is used, as shown in FIG. 13(A), base measurement as a reference is performed, and data of the entire internal region of a circle having the radius R of the k space is acquired. Thereafter, measurement by a concentric blade divided by a concentric circumference centered on the origin of the k space is performed for every predetermined time. At this time, a plurality of concentric blades to be acquired once measure only the low spatial frequency region of the k space, and in the high spatial frequency region, as indicated by a hatched portion in FIG. 13(B), a different region is measured every time by a partial region. A region which is lacking every time uses data of the k space obtained by the base measurement.

With this configuration, k space data with only data of the lower range of the k space updated can be obtained for every predetermined time. Since a single measurement region is small compared to the entire region other than the first time, it is possible to reduce the measurement time. For this reason, it is possible to increase the number of repetitions within the same time and to improve resolution in the time direction of the dynamic measurement.

Second Embodiment

Next, a second embodiment to which the invention is applied will be described. In the first embodiment, although the scan region of the k space is the internal region of the circle centered on the origin, in this embodiment, the scan region is the internal region of an ellipse centered on the origin of the k space.

An MRI apparatus of this embodiment is basically the same as in the first embodiment. Each functional configuration to be implemented by the signal processing system 70 is the same as in the first embodiment, and the imaging process by these functions is the same. However, as described above, in this embodiment, since the internal region of the ellipse of the k space is measured, a gradient magnetic field shape of an imaging sequence for implementing this is different. Hereinafter, this embodiment will be described focusing on a configuration different from the first embodiment.

In this embodiment, an elliptical k space is measured with measurement by the fan-shaped blade 320. Accordingly, rectangular resolution measurement and/or rectangular perimetry which cannot be implemented in the non-orthogonal system measurement of the related art can be performed.

Figure 14:
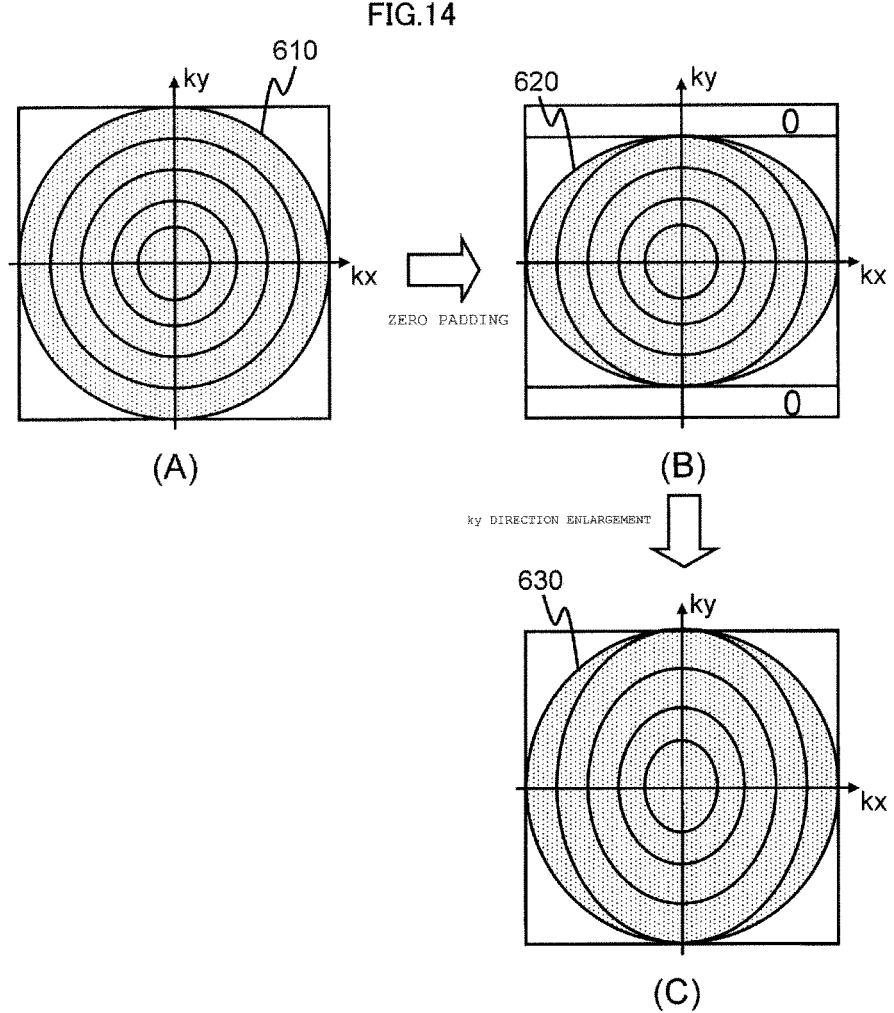
FIGS. 14(A) to 14(C) are explanatory views illustrating rectangular resolution measurement and rectangular perimetry.

FIG. 14(A) shows a perfect circular k space measurement of the related art in which a perfect circular k space 610 with the same number of encodes in the kx direction and the ky direction is measured. As shown in FIG. 14(B), the rectangular resolution measurement is a measurement which is made while changing the number of encodes in the kx direction and the ky direction with respect to the perfect circular k space measurement. As shown in FIG. 14(B), implementation is made by a zero padding measurement using a zero padded k space 620. Accordingly, spatial resolution in the x direction and spatial resolution in the y direction are different from each other.

The rectangular perimetry is a method in which the field of vision in the kx direction and the ky direction changes and the measurement time is reduced without causing a decrease in spatial resolution. Implementation is made by an expanded pitch measurement using an expanded pitch k space 630 shown in FIG. 14(C) obtained by expanding the zero padded k space 620 shown in FIG. 14(B) in the ky direction as a perfect circle. Typically, the field of vision in the phase encode direction decreases, thereby reducing the measurement time without causing a decrease in spatial resolution.

Figure 15:
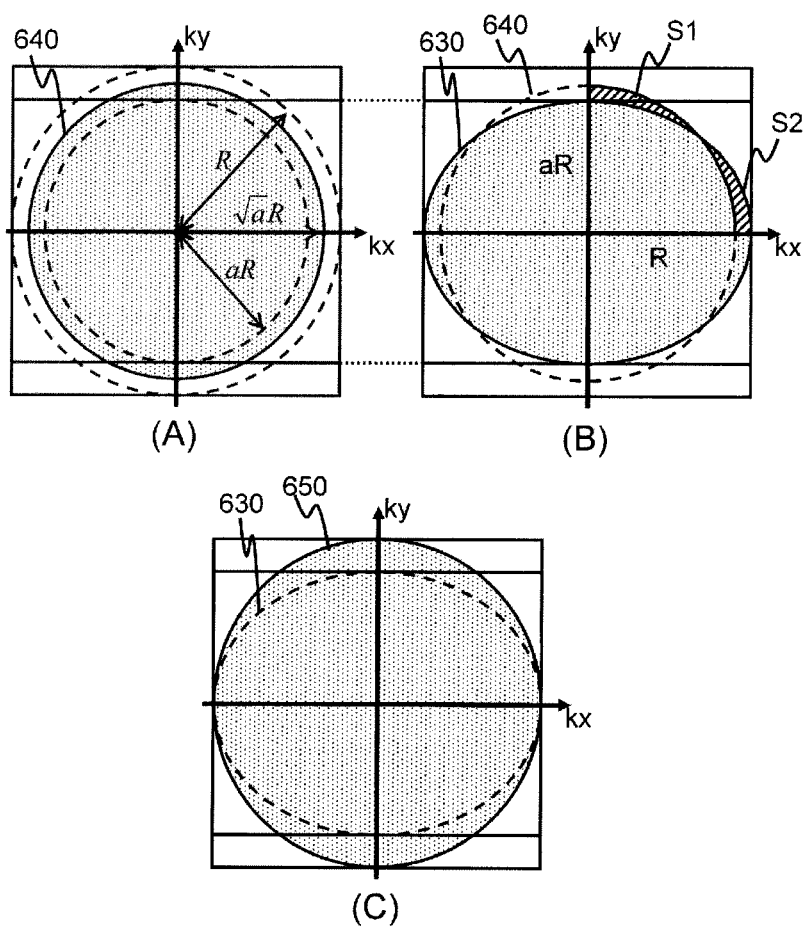
FIGS. 15(A) to 15(C) are explanatory views illustrating rectangular resolution measurement and rectangular perimetry of a second embodiment.

Hereinafter, a gradient magnetic field waveform which implements a rectangular resolution measurement will be described. First, a method which creates the zero padded k space 620 shown in FIG. 14(B) will be described. Here, as shown in FIG. 15(B), it is assumed that the zero padded k space 620 is an internal region (elliptical k space) 640 of an ellipse having a major radius R and a minor radius R' (R'=aR<R, 0.0<a<1.0, a: ellipticity).

The total number $B_{fan}$ of fan-shaped blades 320 necessary for filling the internal region of the elliptical k space 640 is obtained by Expression (15).

[Equation 15]

$$B_{fan} = \frac{\pi R R'}{FP} \qquad (15)$$
$$= \frac{\pi R \cdot aR}{FP}$$
$$= \frac{a\pi}{4} \frac{F}{P}$$

A perfect circular k space 650 having a radius $\sqrt{a}R$ shown in FIG. 15(A) is considered as a perfect circular k space having the same area as the elliptical k space 640. A scan track for filling the perfect circular k space 650 is obtained by Expression (6) to Expression (12) in the first embodiment.

If the scan track obtained in the perfect circular k space 650 is applied to the elliptical k space 640, a region (outer region S1) where a perfect circle is outside an ellipse and a region (inner region S2) where an ellipse is outside a perfect circle are generated in each quadrant of the k space. The outer region S1 and the inner region S2 have the same area.

In the fan-shaped blade 320 including the outer region S1, since a perfect circle is outside an ellipse, a track for scanning the outer region S1 in the scan track obtained in the perfect circular k space 650 is not required. In the fan-shaped blade 320 including the inner region 52, since an ellipse is outside a perfect circle, the inner region 52 cannot be filled only with the scan track obtained in the perfect circular k space 650. Accordingly, in this embodiment, the scan track of the outer region S1 of the fan-shaped blade 320 including the outer region S1 is allocated to scanning of the inner region S2 of the fan-shaped blade 320 including the inner region S2, thereby eliminating excess and deficiency of the track.

Specifically, a transformation matrix is created from the geometric relationship between the outer region S1 and the inner region S2 and applied to the track of the outer region S1 to obtain the track of the inner region S2. If the outer region S1 and the inner region S2 are respectively represented by vectors $p_1$ and $p_2$, the vectors $p_1$ and $p_2$ are expressed by Expression (16) using a transformation matrix T.

[Equation 16]

$$p_2 = Tp_1 \qquad (16)$$

From Expression (16), the transformation matrix T is expressed by Expression (17).

[Equation 17]

$$T = p_2 p_1^T (p_1 p_1^T)^{-1} \qquad (17)$$

Here, the vectors $p_1$ and $p_2$ are respectively expressed by Expression (18) and Expression (19). Vectors q and r respectively represent an inner boundary and an outer boundary between the outer region S1 and the inner region S2. Vectors x and y are respectively unit vectors parallel to the kx axis and the ky axis.

[Equation 18]

$$p_1 = sq_1 + tr_1 (\text{where, } s+t=1) \qquad (18)$$

or, $$q_1 = \alpha_1 x + \beta_1 y \left(\text{where, } \alpha_1^2 + \beta_1^2 = aR^2, \sqrt{\frac{a}{a+1}} R \leq \alpha_1 < \sqrt{a} R\right)$$

$$r_1 = \gamma_1 x + \delta_1 y \left(\text{where, } \gamma_1^2 + \frac{\delta_1^2}{a^2} = R^2, \frac{\beta_1}{\alpha_1} = \frac{\delta_1}{\gamma_1}\right)$$

[Equation 19]

$$p_2 = uq_2 + vr_2 (\text{where, } u+v=1) \qquad (19)$$

or, $$q_2 = \alpha_2 x + \beta_2 y \left(\text{where, } \alpha_2^2 + \frac{\beta_2^2}{a^2} = R^2, 0 \leq \alpha_2 < \sqrt{\frac{a}{a+1}} R\right)$$

$$r_2 = \gamma_2 x + \delta_2 y \left(\text{where, } \gamma_2^2 + \delta_2^2 = aR^2, \frac{\beta_2}{\alpha_2} = \frac{\delta_2}{\gamma_2}\right)$$

The sequence creation unit 720 of this embodiment uses the transformation matrix T and determines a gradient magnetic field waveform such that, when measuring the fan-shaped blade 320 including the outer region S1, the corresponding inner region S2 is scanned.

As shown in FIG. 15(C), the rectangular perimetry is implemented by expanding the zero padded k space 620 (elliptical k space 640) in the ky direction. Specifically, the measurement control unit 730 performs a measurement according to a sequence created by the method of the above-described rectangular resolution measurement. The image reconstruction unit 740 expands the obtained k space (zero padded k space 620 (elliptical k space 640)) in the ky direction (expanded k space 660) and then performs gridding process to reconstruct an image.

If the zero padded k space 620 is expanded in the ky direction, a k space (expanded k space 660) in which a pitch Δky in the ky direction is expanded 1/a (>1.0) times greater than the kx direction is obtained. Since the k space pitch and the imaging field of vision (FOV) have a relationship shown in Expression (20), if the k space (expanded k space 660) after expansion is used, the imaging field of vision has a rectangular shape which is short in the y direction.

[Equation 20]

$$FOV_y = \frac{1}{\Delta ky} \qquad (20)$$

As described above, according to this embodiment, as in the first embodiment, the elliptical k space is measured using the fan-shaped blade. Accordingly, in addition to the effects of the first embodiment, the rectangular resolution measurement and/or the rectangular perimetry which cannot be implemented in the non-orthogonal system measurement of the related art can be performed. Therefore, a degree of freedom for imaging increases.

In this embodiment, as in the first embodiment, any echo arrangement order may be used insofar as an echo signal for desired TE (effective TE) can be arranged in the low spatial frequency region of the k space, and any of centering, uncentering, echo shift, and the like may be used. A multi-contrast measurement may be applied. A half measurement may be applied. A combination with blades having different shapes may be made.

In the foregoing embodiments, although the signal processing system 70 of the MRI apparatus 100 may be configured so as to calculate the gradient magnetic field waveform implementing k space scan with the fan-shaped blades from the imaging conditions, the invention is not limited thereto. A configuration may be made such that a gradient magnetic field waveform is calculated on an information processing apparatus which can perform data transmission and reception with the MRI apparatus 100 and is separated from the MRI apparatus.

In the foregoing embodiments, although the sequence creation unit 720 calculates the parameters of the fan-shaped blades using the imaging parameters each time the imaging parameter is set during imaging and calculates the gradient magnetic field shape, the invention is not limited thereto. For example, a configuration may be made such that the gradient magnetic field shape is calculated in advance for each imaging parameter which is likely to be used and stored as a database in the storage device 72 or the like in association with the imaging parameter. In this case, if the imaging parameter is received during imaging, in Step S1102, the sequence creation unit 720 extracts the gradient magnetic field shape stored in association with the received imaging parameter with reference to the database and creates an imaging sequence.

In the foregoing embodiments, although the unit region is a fan-shaped region which is surrounded by two radii R and an arc between both radii R of the circle having the radius R centered on the origin of the k space, the invention is not limited thereto. The unit region may be a region which is surrounded by two line segments with the origin of the k space as a starting point and a line connecting the other end points of the two line segments.

In the foregoing embodiments, the unit region is divided into a plurality of divided regions at different positions in the radial direction, and the measurement control unit acquired a plurality of pieces of data for each of a plurality of divided regions. The measurement control unit acquires each piece of data while sequentially changing the track in the circumferential direction and the position in the radial direction inside the divided region. However, the measurement control unit may acquire each piece of data while sequentially changing the track in a direction perpendicular to the radial direction and the position in the radial direction inside the divided region. The track in the circumferential direction or the track in the direction perpendicular to the radial direction may have or not have a connection portion (a portion in which data is continuously acquired) between adjacent tracks.

REFERENCE SIGNS LIST

10: object, 20: static magnetic field generation system, 30: gradient magnetic field generation system, 31: gradient magnetic field coil, 40: sequencer, 50: transmission system, 51: transmission coil, 52: synthesizer, 53: modulator, 54: high-frequency amplifier, 60: reception system, 61: reception coil, 62: signal amplifier, 63: orthogonal phase detector, 64: A/D converter, 70: signal processing system, 71: CPU, 72: storage device, 73: external storage device, 74: display device, 75: input device, 100: MRI apparatus, 210: imaging sequence, 211: excitation RF pulse, 212: reconvergence RF pulse, 213: gradient magnetic field, 214: gradient magnetic field, 220: imaging sequence, 223: gradient magnetic field, 224: gradient magnetic field, 310: rectangular blade, 32: gradient magnetic field power supply, 320: blade, 320: fan-shaped blade, 321: divided region, 510: linear track, 520: pendulum-like track, 521: arc-like track, 522: linear track, 610: perfect circular k space, 620: zero padded k space, 630: expanded pitch k space, 640: elliptical k space, 650: perfect circular k space, 660: expanded k space, 710: reception unit, 720: sequence creation unit, 730: measurement control unit, 740: image reconstruction unit

The invention claimed is:

1. A magnetic resonance imaging apparatus comprising:
a static magnetic field generation unit which generates a static magnetic field;
a magnetic field application unit which applies a gradient magnetic field and a high-frequency magnetic field to a desired imaging region of an object arranged in the static magnetic field;
a detection unit which detects an echo signal from the desired imaging region;
a measurement control unit which controls the magnetic field application unit and the detection unit and measures the echo signal so as to acquire data of a predetermined region inside k space; and
an image reconstruction unit which reconstructs an image of the imaging region using data of the k space,
wherein the measurement control unit performs control such that a unit measurement to acquire a plurality of pieces of data of a unit region for 1 TR is repeated while rotating the unit region at a rotation angle determined in advance centered on the origin of the k space for each unit measurement,
in the unit measurement, an echo signal having desired contrast is arranged in a low spatial frequency region of the k space, and
the unit region is a region which is surrounded by two line segments with the origin of the k space as a starting point and a line connecting the other end points of the two line segments, and
wherein the two line segments are the radius of a circle centered on the k space, and
the line connecting the end points is an arc of the circle, and
wherein the rotation angle of each unit region is determined such that the unit region is arranged in a circumferential direction of the circle centered on the origin of the k space without overlapping, and
wherein, in the unit measurement, when a unit region to be subjected to the unit measurement includes a region inside an internal region of the circle outside an internal region of an ellipse such that the radius of the circle corresponds to a square root multiple of ellipticity, the measurement control unit performs control so as to acquire data of a region having the same area of a different unit region inside an external region of the ellipse outside the internal region of the circle, instead of scanning the region.

2. A magnetic resonance imaging apparatus comprising:
a static magnetic field generation unit which generates a static magnetic field;
a magnetic field application unit which applies a gradient magnetic field and a high-frequency magnetic field to a desired imaging region of an object arranged in the static magnetic field;

a detection unit which detects an echo signal from the desired imaging region;

a measurement control unit which controls the magnetic field application unit and the detection unit and measures the echo signal so as to acquire data of a predetermined region inside k space; and an image reconstruction unit which reconstructs an image of the imaging region using data of the k space, wherein the measurement control unit performs control such that a unit measurement to acquire a plurality of pieces of data of a unit region for 1 TR is repeated while rotating the unit region at a rotation angle determined in advance centered on the origin of the k space for each unit measurement, in the unit measurement, an echo signal having desired contrast is arranged in a low spatial frequency region of the k space, and the unit region is a region which is surrounded by two line segments with the origin of the k space as a starting point and a line connecting the other end points of the two line segments, and wherein the two line segments are the radius of a circle centered on the k space, and the line connecting the end points is an arc of the circle, and wherein the magnetic resonance imaging apparatus further comprises:

an imaging condition reception unit which receives an imaging condition from an operator; and an imaging sequence generation unit which generates an imaging sequence from the received imaging condition, wherein the measurement control unit performs the control according to the imaging sequence, and the imaging sequence generation unit includes a parameter determination unit which determines the radius of the circle centered on the origin of the k space, a central angle as the angle between the two line segments, and the total number of unit regions which is the number of unit regions having different rotation angles, a region determination unit which determines an arrangement region of each echo signal for each unit measurement, a scan track determination unit which determines a scan track inside each determined arrangement region, and a waveform determination unit which determines the scan track of each unit measurement according to a rotation angle of each unit region and determines the gradient magnetic field waveform of the imaging sequence, and wherein the region determination unit arranges each echo signal according to one of centric arrangement, reverse centric arrangement and echo shift arrangement.

3. The magnetic resonance imaging apparatus according to claim 2, wherein the radius of the circle centered on the origin of the k space is determined by the number of frequency encodes, the central angle is determined by the diameter of the circle and the total number of pieces of data inside the unit region, and the total number of unit regions is equal to or greater than a value obtained by dividing $2\pi$ by the central angle.

4. A magnetic resonance imaging apparatus comprising:

a static magnetic field generation unit which generates a static magnetic field;

a magnetic field application unit which applies a gradient magnetic field and a high-frequency magnetic field to a desired imaging region of an object arranged in the static magnetic field;

a detection unit which detects an echo signal from the desired imaging region;

a measurement control unit which controls the magnetic field application unit and the detection unit and measures the echo signal so as to acquire data of a predetermined region inside k space; and an image reconstruction unit which reconstructs an image of the imaging region using data of the k space, wherein the measurement control unit performs control such that a unit measurement to acquire a plurality of pieces of data of a unit region for 1 TR is repeated while rotating the unit region at a rotation angle determined in advance centered on the origin of the k space for each unit measurement, in the unit measurement, an echo signal having desired contrast is arranged in a low spatial frequency region of the k space, and the unit region is a region which is surrounded by two line segments with the origin of the k space as a starting point and a line connecting the other end points of the two line segments, and wherein the two line segments are the radius of a circle centered on the k space, and the line connecting the end points is an arc of the circle, and wherein the magnetic resonance imaging apparatus further comprises:

an imaging condition reception unit which receives an imaging condition from an operator; and an imaging sequence generation unit which generates an imaging sequence from the received imaging condition, wherein the measurement control unit performs the control according to the imaging sequence, and the imaging sequence generation unit includes a parameter determination unit which determines the radius of the circle centered on the origin of the k space, a central angle as the angle between the two line segments, and the total number of unit regions which is the number of unit regions having different rotation angles, a region determination unit which determines an arrangement region of each echo signal for each unit measurement, a scan track determination unit which determines a scan track inside each determined arrangement region, and a waveform determination unit which determines the scan track of each unit measurement according to a rotation angle of each unit region and determines the gradient magnetic field waveform of the imaging sequence, and wherein the waveform determination unit determines the gradient magnetic field waveform after the scan track of each unit measurement is determined and after the entire k space is extended by a predetermined amount in an axial direction of the k space.

5. The magnetic resonance imaging apparatus according to claim 4, wherein the rotation angle of each unit region is determined such that the unit region is arranged in a region having an area half the circle centered on the origin of the k space.

6. The magnetic resonance imaging apparatus according to claim 4, wherein the scan track inside each arrangement region is like a pendulum.

7. A magnetic resonance imaging apparatus comprising:

a static magnetic field generation unit which generates a static magnetic field;

a magnetic field application unit which applies a gradient magnetic field and a high-frequency magnetic field to a desired imaging region of an object arranged in the static magnetic field;

a detection unit which detects an echo signal from the desired imaging region;

a measurement control unit which controls the magnetic field application unit and the detection unit and measures the echo signal so as to acquire data of a predetermined region inside k space; and an image reconstruction unit which reconstructs an image of the imaging region using data of the k space, wherein the measurement control unit performs control such that a unit measurement to acquire a plurality of pieces of data of a unit region for 1 TR is repeated while rotating the unit region at a rotation angle determined in advance centered on the origin of the k space for each unit measurement, in the unit measurement, an echo signal having desired contrast is arranged in a low spatial frequency region of the k space, and the unit region is a region which is surrounded by two line segments with the origin of the k space as a starting point and a line connecting the other end points of the two line segments, and wherein the unit region is divided into a plurality of divided regions at different positions in a radial direction, and the measurement control unit acquires a plurality of pieces of data for each of the plurality of divided regions, and wherein the measurement control unit acquires each piece of data while sequentially changing a track in a circumferential direction and a position in a radial direction inside each divided region.

8. A magnetic resonance imaging apparatus comprising:

a static magnetic field generation unit which generates a static magnetic field;

a magnetic field application unit which applies a gradient magnetic field and a high-frequency magnetic field to a desired imaging region of an object arranged in the static magnetic field;

a detection unit which detects an echo signal from the desired imaging region;

a measurement control unit which controls the magnetic field application unit and the detection unit and measures the echo signal so as to acquire data of a predetermined region inside k space; and an image reconstruction unit which reconstructs an image of the imaging region using data of the k space, wherein the measurement control unit performs control such that a unit measurement to acquire a plurality of pieces of data of a unit region for 1 TR is repeated while rotating the unit region at a rotation angle determined in advance centered on the origin of the k space for each unit measurement, in the unit measurement, an echo signal having desired contrast is arranged in a low spatial frequency region of the k space, and the unit region is a region which is surrounded by two line segments with the origin of the k space as a starting point and a line connecting the other end points of the two line segments, and wherein the unit region is divided into a plurality of divided regions at different positions in a radial direction, and the measurement control unit acquires a plurality of pieces of data for each of the plurality of divided regions, and wherein the measurement control unit acquires each piece of data while sequentially changing a track in a direction perpendicular to a radial direction and a position in the radial direction inside each divided region.

9. An echo signal measurement method in a magnetic resonance imaging apparatus, a static magnetic field generation unit which generates a static magnetic field, a magnetic field application unit which applies a gradient magnetic field and a high-frequency magnetic field to a desired imaging region of an object arranged in the static magnetic field, a detection unit which detects an echo signal from the desired imaging region, a measurement control unit which controls the magnetic field application unit and the detection unit and measures the echo signal so as to acquire data of a predetermined region inside k space, and an image reconstruction which reconstructs an image of the imaging region using data of the k space, wherein the echo signal measurement method comprises:

(a) performing, by the measurement control unit, unit measurement which acquires, as unit data, data of a unit region surrounded by two line segments with the origin of a k space as a starting point and a line connecting the other end points of the two line segments; and (b) performing, by the measurement control unit, repetitive measurement which repeats performing the unit measurement of (a) while rotating the unit region at a rotation angle determined in advance centered on the origin; and acquiring, by the measurement control unit, each piece of data while sequentially changing a track in a circumferential direction and a position in a radial direction inside each divided region.

* * * * *